(12) United States Patent
Hunger et al.

(10) Patent No.: US 9,891,151 B2
(45) Date of Patent: Feb. 13, 2018

(54) DRILLING-RESISTANCE MEASURING DEVICE FOR USE UNDERWATER

(71) Applicant: IML Instrumenta Mechanik Labor GmbH, Wiesloch (DE)

(72) Inventors: Erich Hunger, Karlsruhe (DE); Sebastian Hunger, Wiesloch (DE); Fabian Hunger, Leimen (DE)

(73) Assignee: IML Instrumenta Mechanik Labor GmbH, Wiesloch (DE)

( * ) Notice: Subject to any disclaimer, the term of this patent is extended or adjusted under 35 U.S.C. 154(b) by 23 days.

(21) Appl. No.: 15/125,169

(22) PCT Filed: Aug. 20, 2015

(86) PCT No.: PCT/EP2015/001708
§ 371 (c)(1),
(2) Date: Sep. 11, 2016

(87) PCT Pub. No.: WO2016/041617
PCT Pub. Date: Mar. 24, 2016

(65) Prior Publication Data
US 2017/0184480 A1 Jun. 29, 2017

(30) Foreign Application Priority Data
Sep. 16, 2014 (DE) .................. 10 2014 013 412

(51) Int. Cl.
*G01N 3/58* (2006.01)

(52) U.S. Cl.
CPC ....... *G01N 3/58* (2013.01); *G01N 2203/0053* (2013.01); *G01N 2203/0236* (2013.01)

(58) Field of Classification Search
CPC .. G01N 3/04; G01N 3/40; G01N 3/58; G01N 33/46; G01N 33/0098; G01N 2203/0053; G01N 2203/0076; G01N 19/00
(Continued)

(56) References Cited

U.S. PATENT DOCUMENTS 6,290,437 B1 * 9/2001 Mattheck .................. B25F 3/00
408/11
2006/0147284 A1 7/2006 Kim
(Continued)

FOREIGN PATENT DOCUMENTS

DE 100 31 334 A1 1/2001
DE 100 31 395 A1 4/2001

*Primary Examiner* — Peter Macchiarolo
*Assistant Examiner* — Nathaniel Kolb
(74) *Attorney, Agent, or Firm* — Gudrun E. Huckett (57) ABSTRACT

The invention relates to a drilling-resistance measuring device (10) and to a method for material testing in a humid environment or underwater. The drilling-resistance measuring device (10) comprises a housing (1), in which a drive and a drill chuck (3) coupled to the drive are arranged, in which drill chuck a drilling needle (4) is or can be releasably held, wherein the housing (1) has a drilling-needle outlet opening (5') enclosed by a drilling-needle outlet guide (5), through which drilling-needle outlet opening the drilling needle (4) extends out of the housing (1). The drilling-resistance measuring device (10) comprises at least one water-tight bellows (6), which is arranged in the interior of the housing (1) around the drilling needle (4) between the drill chuck (3) and the drilling-needle outlet guide (5), wherein moisture or water can enter the bellows (6) through the drilling-needle outlet opening (5').

18 Claims, 9 Drawing Sheets

(58) Field of Classification Search
USPC .............................................................. 73/85
See application file for complete search history.

(56) References Cited

U.S. PATENT DOCUMENTS

| | | | |
|---|---|---|---|
| 2012/0139739 A1* | 6/2012 | Bishop | B23B 51/00 340/657 |
| 2013/0104634 A1* | 5/2013 | Hunger | G01N 1/08 73/85 |
| 2014/0109660 A1* | 4/2014 | Hunger | G01N 33/0098 73/82 |
| 2015/0233806 A1* | 8/2015 | More | G01N 3/42 73/85 |
| 2016/0221087 A1* | 8/2016 | Hunger | B23B 31/005 |

* cited by examiner

DRILLING-RESISTANCE MEASURING DEVICE FOR USE UNDERWATER

BACKGROUND OF THE INVENTION

The invention concerns a drilling resistance measuring device for material testing that is provided for work and use in humid environment, in particular also under water. The drilling resistance measuring device comprises a housing in which a drive and a drill chuck, coupled with the drive and provided with a drilling needle detachably arranged therein, are arranged, wherein the housing comprises a drilling needle outlet opening which is surrounded by a drilling needle outlet guide and through which the drilling needle extends out of the housing.

For performing drilling resistance measurements by means of which material properties in the interior of test bodies are derived, drilling resistance measuring devices with thin drilling tools or drilling needles are used. The drilling needle is moved by a drive of the drilling resistance measuring device and driven into the test body wherein, for example, the power input or the current consumption of the drive is used as a measure for the drilling resistance of the test body upon penetration or removal of the drilling needle and correlated, for example, with the penetration depth of the drilling needle so that the material properties in the interior of the test body can be assessed.

In case of measurements in humid environment, for example, in pouring rain or under water, penetration of moisture or water into the drilling resistance measuring device is to be prevented in order to avoid damaging the drive.

DE 100 31 334 A1 discloses in this context a drilling resistance measuring device that comprises an outlet opening for the drilling needle and means for generating an increased gas pressure in the interior of the drilling resistance measuring device so that the pressure present in the interior of the drilling resistance measuring device corresponds to a simultaneously measured outer pressure and no water can penetrate into the interior of the drilling resistance measuring device. The means for generating an increased inner gas pressure can be a pressurized gas line coupled with the interior of the drilling resistance measuring device or an attached gas cartridge.

Based on this prior art, it is the object of the present invention to provide a drilling resistance measuring device that is functioning in humid environment and under water independent of a pressurized gas source.

SUMMARY OF THE INVENTION

This object is solved by a drilling resistance measuring device that comprises at least one water-tight bellows which is arranged in the interior of the housing around the drilling needle between the drill chuck and the drilling needle outlet guide, wherein through the drilling needle outlet opening moisture or water can enter the bellows.

Further embodiments are disclosed in the dependent claims.

The further object of providing a method for performing a drilling resistance measurement in humid environment or under water without utilizing a pressurized gas source is solved by the method for drilling resistance measurement with a drilling resistance measuring device of the present invention, comprising the steps:

attaching the drilling resistance measuring device in humid environment or under water to an object to be tested, in doing so allowing moisture or water to penetrate through the drilling needle outlet opening into the at least one bellows;

advancing and inserting the drilling needle into the object to be tested, in doing so pushing together the at least one bellows, and, upon reaching a predetermined pressure within the pushed-together bellows, allowing moisture or water to exit into the environment of the drilling resistance measuring device, preferably by opening a valve device which is in communication with the interior of the at least one bellows and the environment.

A drilling resistance measuring device according to the invention for material testing in humid environment or under water comprises a housing in which a drive and a drill chuck, which is coupled therewith and in which a drilling needle is received or can be received detachably, are arranged. Moreover, the housing comprises a drilling needle outlet opening that is surrounded by a drilling needle outlet guide through which the drilling needle received in the drill chuck is extending out of the housing. According to the invention, the drilling resistance measuring device comprises at least one water-tight bellows which is arranged in the interior of the housing between the drill chuck and the drilling needle outlet guide around the drilling needle which is received or can be received in the drill chuck, wherein moisture or water can penetrate through the drilling needle outlet opening into the bellows without the electrical drive and measuring devices in the housing being impaired in their function by moisture. According to the invention, it is permitted that the drilling needle is running in water within the bellows; a pressurized gas source is obsolete.

The bellows can be connected sealingly with one end around the drill chuck to a drive housing within the housing and with the other end around the drilling needle outlet opening to the drilling needle outlet guide or to the surrounding housing section.

When, as a function of the length of the drilling needle and the type of bellows, the arrangement of more than one bellows between the drill chuck and the drilling needle outlet guide is provided, the bellows are arranged in series one after another and connected with each other by an adapter piece, respectively, which also serves for stabilizing the bellows when pushed together during advancement of the drilling needle for performing the drilling resistance measurement.

Since water penetration into the bellows is permissible, it is advantageous to employ a contact-free operative connection between the drive and the drill chuck so that at this location the drive can be sealed relative to moisture. For this purpose, the drill chuck and the drive are connected by means of a coupling device which enables a contact-free torque transmission from the drive to the drill chuck. This is preferably a magnetic coupling device in which a drive-associated magnetic coupling partner is operatively connected without contact with a drill chuck-associated magnetic coupling partner which, for this purpose, comprises a hollow-cylindrical magnetic holder for a receiving element of the drill chuck for the drilling needle.

The drill chuck comprises moreover one or several clamping bodies and a clamping insert which, in turn, comprises one or several counter bodies that supplements or supplement the clamping body or clamping bodies when it or they is/are arranged in a recess on a cylindrical section of the receiving element. The counter body or bodies extends/extend away from a contact disk of the clamping insert which is resting against an end face of the cylindrical section when the counter bodies are received in the recess of the receiving element. The contact disk is provided with a through opening for the drilling needle which is received or is to be received between counter body and clamping body. In regard to dimensions and shape, counter bodies and clamping bodies are therefore designed for arrangement in the recess and for a clamping receiving action of a flattened end section of the drilling needle between the clamping body(ies) and the counter bodies. Due to the flat surface, the drilling needle which is detachably received in the drilling needle receptacle is secured against slip.

In order to compensate or make tolerable the imbalance which is caused upon rotation by the flattened end section of the drilling needle such that the concentric arrangement of the drilling needle relative to a drive shaft of the drive device is not impaired and the drilling needle rotates about the same axis of rotation as the motor drive shaft, the coupling device of the drill chuck is designed as a magnetic coupling.

The hollow-cylindrical magnetic holder for the receiving element can be, for example, formed by an annular magnet which is arranged spaced apart and contact-free coaxially around the cylindrical section of the receiving element. Preferably, in this context a magnetically affectable spacer ring can surround the cylindrical section so that the magnetic holder can act on the receiving element.

The contact-free magnetic coupling of the drilling needle receiving device with the drive device and the contact-free arrangement of the receiving element in the drill chuck enable a certain imbalanced rotation of the receiving element in which the flattened end section is received, wherein, depending on where the imbalance is presently occurring, one of the clamping bodies in the cage which is formed of the counter bodies of the clamping insert takes on the clamping action of the drilling needle, respectively.

In a preferred embodiment, it is provided that the drilling resistance measuring device comprises a valve device through which upon advancement of the drilling needle, which is associated with pushing together the bellows, for performing a drilling resistance measurement the water collected within the interior of the bellows is allowed to exit into the environment when a certain pressure is reached. For this purpose, the valve device is in fluidic communication with the bellows interior and the environment of the drilling resistance measuring device and can be preferably provided on the drilling needle outlet guide or on the housing around the drilling needle outlet guide. This valve device opens in one direction in order to enable escape of water from the interior of the bellows into the environment upon reaching a predetermined pressure in the bellows interior and blocks in the opposite direction, at least up to a certain predetermined (second) pressure so that, upon retraction of the drilling needle with the associated pulling apart of the bellows after completion of the drilling resistance measurement water cannot penetrate—or can only penetrate beginning at a certain vacuum that is produced in the interior of the bellows by the pulling apart action and that depends on the retraction speed—through the valve device, but only through the drilling needle outlet opening, into the interior of the bellows. When no valve device is provided, the water is pressed out of the interior of the bellows through the drilling needle outlet opening upon pushing together the bellows. The action of pushing together the bellows can in both cases, i.e., with and without valve device, be assisted by the drive of the drilling resistance measuring device; the increased power input with no valve device, which is also dependent on the depth of use under water, can be taken into consideration for the drilling resistance measurement.

For improving the centered guiding action of the drilling needle between the drill chuck and the drilling needle outlet guide, a drilling resistance measuring device according to the invention can comprise a telescoping guiding device of a plurality of cup-shaped tube sections of different diameters in which the drilling needle is guided. Such a telescoping guiding device is arranged within the at least one bellows so that it is also extending between the drill chuck and the drilling needle outlet guide around the drilling needle. Also, a telescoping guiding device prevents buckling of the bellows upon being pushed together or upon advancement of the drilling needle.

Due to the fact that penetration of moisture/water through the drilling needle outlet opening is permitted, a guide sleeve without special sealing means at the through opening can be used in the drilling needle outlet guide. On the other hand, due to the centering receiving action in the drill chuck a diameter of the through opening at the guide sleeve can be selected to be almost corresponding to the diameter of the drilling needle so that between the drilling needle and the wall of the through opening in the guide sleeve a minimal gap is present. The gap width should be at most 5%, preferably 1% to 2%, of the drilling needle diameter. Advantageously, upon retraction of the drilling needle from the test object and into the housing, no or hardly any dirt, for example, removed material of the test object, reaches the housing interior through this gap; instead, material residues are stripped off by the drilling needle outlet guide upon retraction of the drilling needle. A preferred drilling needle diameter is approximately maximally 3 mm, preferably 1.5 mm, in order to keep the damages that are possibly produced by the invasive drilling resistance measurement as small as possible.

Usually, such drilling resistance measuring devices comprise also a device for acquiring the drilling resistance as well as a device for processing, storing, and outputting the acquired or processed measured values. In this context, for performing underwater measurements it may be expedient to provide the device for acquiring the drilling resistance within the housing and the device for processing, storing, and outputting the acquired drilling resistance values outside of the housing. The latter can then be connected with the device for acquiring the drilling resistance by cable or wireless, for example, by a radio connection.

The drilling resistance measuring device can comprise in a further embodiment a rechargeable battery pack for supply of the drive with electrical energy which comprises an electrical connector and a locking section. On the housing of the drilling resistance measuring device itself, a corresponding electrical connector and also a corresponding counter locking section are present. In an engaging arrangement of rechargeable battery pack and housing, the locking section of the rechargeable battery pack engages the counter locking section of the drilling resistance measuring device and the electrical connectors of the rechargeable battery pack and of the drilling resistance measuring device are contacting each other directly. Particularly advantageously, the battery pack can however be decoupled from the housing so that the drive unit can work and measure in an environment that is humid or laden with dust, while the current or energy supply can however be spaced apart from the measuring location and positioned in a dry and protected environment. In this decoupled arrangement, the locking section of the rechargeable battery pack is released from the counter locking section of the drilling resistance measuring device and the electrical connector of the rechargeable battery pack is connected by a cable with the electrical connector of the drilling resistance measuring device.

In yet another embodiment of the drilling device it may comprise in the drive section a compressor for providing am overpressure in the housing. The compressor is advantageously connected with an air filter.

In a preferred embodiment, an air filter is arranged on the rechargeable battery pack. The rechargeable battery pack and the housing comprise pneumatic connectors which are connected to each other in the engaging arrangement of the rechargeable battery pack with the housing. Advantageously, in this way the air filter can also be positioned in a protected manner when the rechargeable battery pack is decoupled from the housing. The rechargeable battery pack and the compressor are then connected to each other by a hose.

A method according to the invention for drilling resistance measurement with a drilling resistance measuring device in humid environment or under water comprises the following steps:
  attaching the drilling resistance measuring device in humid environment or underwater to an object to be tested, in doing so
  allowing moisture or water to penetrate through the drilling needle outlet opening into that the at least one water-tight bellows which is arranged in the housing of the drilling resistance measuring device between the drilling needle outlet guide and the drill chuck around the drilling needle;
  for performing the actual drilling resistance measurement, advancing and inserting the drilling needle into the object to be tested wherein the at least one bellows is pushed together and upon reaching a predetermined pressure within the pushed-together bellows the moisture or the water is allowed to escape into the environment of the drilling needle measuring device. This can be realized through the drilling needle outlet opening, preferably however by opening a valve device that is in communication with the interior of the at least one bellows and with the environment.

Further embodiments as well as some of the advantages associated with them and with further embodiments will become apparent and will be understood better through the following detailed description with reference to the attached Figures. The Figures are only schematic illustrations of an embodiment of the invention.

BRIEF DESCRIPTION OF THE DRAWINGS

It is shown in this context in.

DESCRIPTION OF PREFERRED EMBODIMENTS

Figure 1:
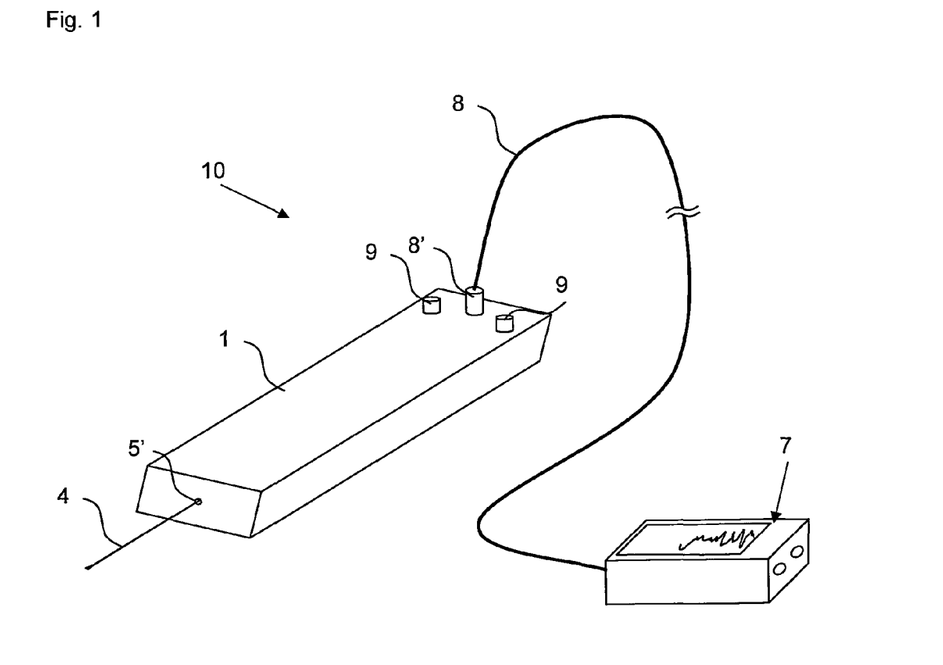
FIG. 1 a perspective view of a drilling resistance measuring device with an electronic unit connected by means of a data cable.

A drilling resistance measuring device 10 according to the invention that is designed for drilling resistance measurement under water but also in very humid environment, but of course can also be used for conventional drilling resistance measurements on land, comprises, as can be seen in FIG. 1, a housing 1 having at its end face a drilling needle outlet opening 5' through which the drilling needle 4 is extending. On the housing 1 a connector 8' for a long data line 8 is provided which is leading to a device 7 for evaluating, storing and/or outputting of the measured drilling resistance values. As an alternative to the line 8, the device 7 can also be connected by means of a wireless communication connection with a device for acquiring the drilling resistance in the interior of the housing 1. Operating elements 9 on the drilling resistance measuring device 10 can be provided, for example, for adjusting drilling or measuring parameters. The supply of the drilling resistance measuring device 10 with energy can be realized by means of batteries, rechargeable batteries or by means of connection to supply mains.

Figure 11:
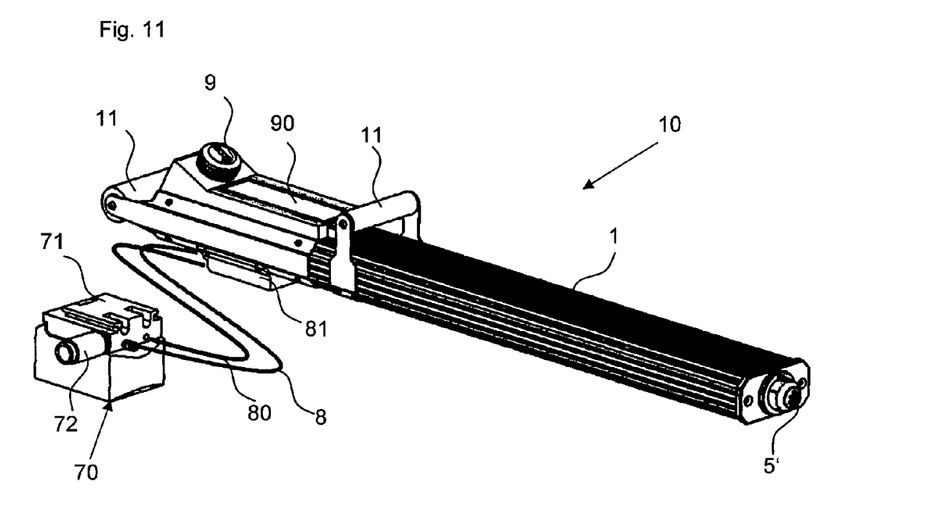
FIG. 11 a perspective view of a drilling resistance measuring device with decoupled rechargeable battery pack connected by cables.
Figure 12:
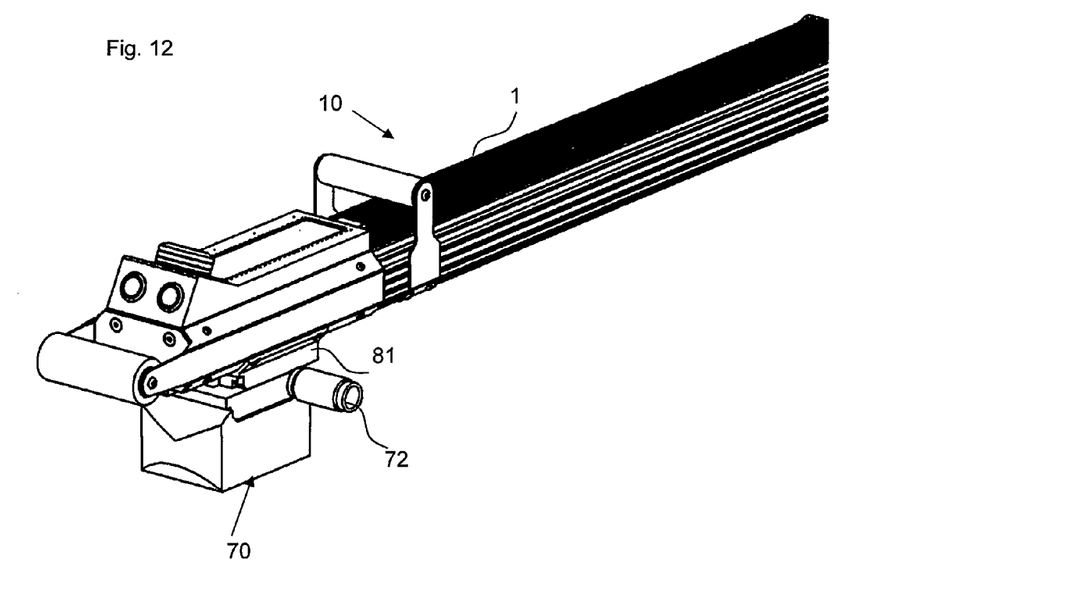
FIG. 12 a perspective view of the drilling resistance measuring device of FIG. 11 with coupled rechargeable battery pack.
Figure 13:
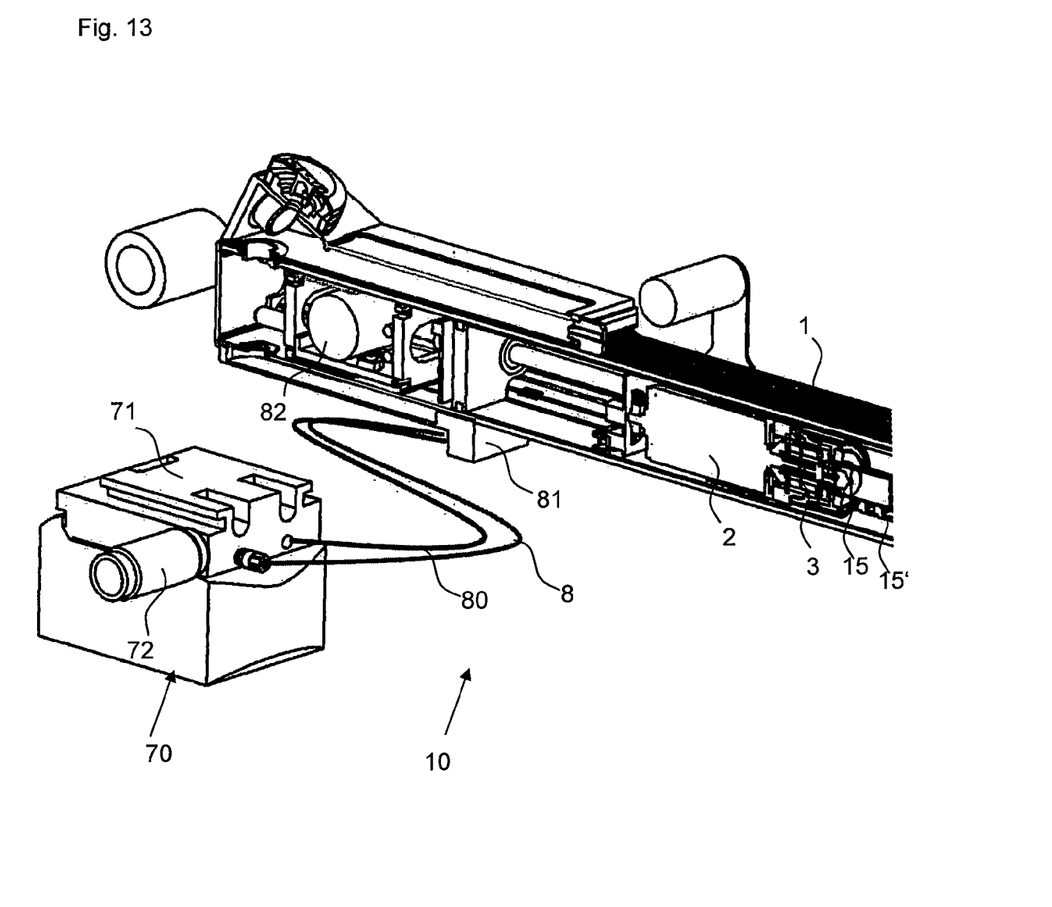
FIG. 13 a perspective partial section view of the drilling resistance measuring device of FIG. 11.

In FIGS. 11 to 13, an embodiment of a drilling resistance measuring device 10 according to the invention is illustrated that comprises a rechargeable battery pack 70 that can be decoupled. In FIGS. 11 and 13, the rechargeable battery pack 70 is decoupled from the housing 1 of the drilling resistance measuring device 10. The power supply of the drilling needle drive in the drive housing 2 is realized by means of an electrical cable 8 by the rechargeable battery pack 70 which can thus be positioned spaced apart from the location of use, for example, outside of the water. The rechargeable battery pack 70 comprises at its topside a locking section 71 which can be brought into engagement with a corresponding counter locking section 81 on the housing 1 of the drilling resistance measuring device 10, as shown in FIG. 12. The locking sections 71,81 are designed such that the electrical connection is produced with locking of the rechargeable battery pack 70 on the housing 1 which both may comprise appropriate connectors (for example, plug and socket). When the rechargeable battery pack 70 is decoupled from the housing, the cable 8 produces the electrical connection; corresponding connectors are provided on the rechargeable battery pack 70 and the housing.

The rechargeable battery pack 70 and the aforementioned computing device 7 can be separate devices but can also be a common device. For data transmission and power supply, two cables 8 may be possibly required.

On the other hand, the data acquired by means of the drilling resistance measuring device 10, when they are not transmitted online by cable or wireless to a spaced-apart device 7, can be, for example, displayed also on a display 90 of the drilling resistance measuring device 10 (see FIG. 11) and/or can be stored in an integrated or insertable storage medium (for example, memory card) that can be connected by a suitable connection or can be connected to a reading device after removal.

Furthermore, in FIGS. 11 and 13 a hose 80 is shown which is extending from the rechargeable battery pack 70 to the housing 1. The hose is in communication with an air filter 72 on the rechargeable battery pack 70 and a compressor 82 in the housing 1 of the drilling resistance measuring device 10. In this context, the rechargeable battery pack 70 also serves for air supply of the drive section of the drilling resistance measuring device 10. The air filter 72 serves for separating fine dust. Due to the separation, the rechargeable battery pack 70 can be positioned in a dry environment and the drilling resistance measuring device 10 can be alternatively used, aside from use under water or in humid environment, also in case of high fine dust loading. The compressor 82 which is housed in the housing 1 generates an overpressure in the drive section so that no fine dust particles and/or moisture can penetrate into it.

It is noted in this context that the embodiment with decoupled rechargeable battery pack 70 is not limited to the variant with compressor. A drilling resistance measuring device 10 according to the invention can also comprise only a rechargeable battery pack 70 that can be decoupled, as illustrated in FIGS. 11 to 13, without this rechargeable battery pack comprising an air filter and without the drilling resistance measuring device comprising a compressor that are connected to each other by a hose.

Figure 2:
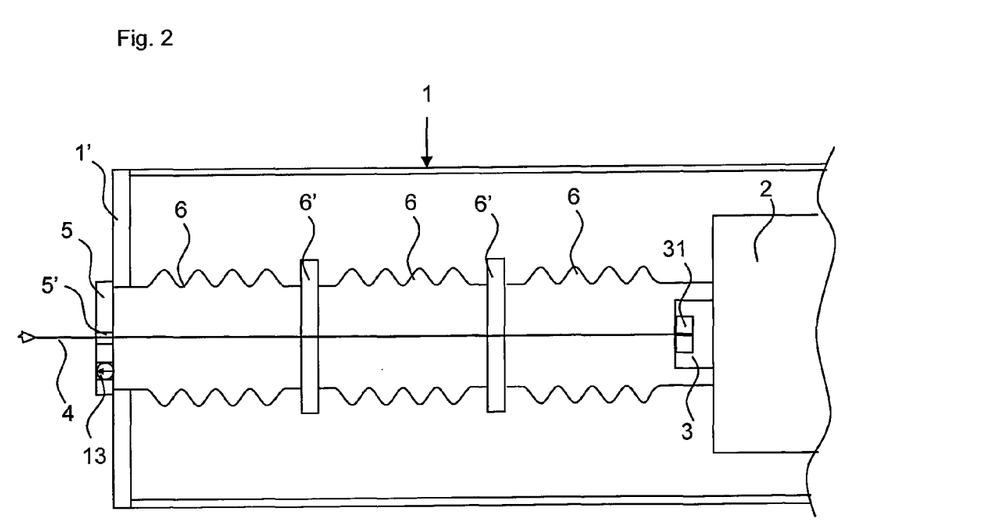
FIG. 2 a schematic sectional side view of a part of a drilling resistance measuring device.

The drilling resistance measuring device 10 according to the invention can be used for performing drilling resistance measurements under water or in a very humid environment without pressurized gas source because in the interior of the housing 1, as indicated in FIG. 2, a bellows arrangement, here comprised of three bellows 6, is arranged between the drilling needle outlet guide 5, illustrated in simplified form, and the drill chuck 3. The bellows 6, manufactured watertight, for example, of rubber, plastic material, or silicone, are connected to each other by stabilizing adapter pieces 6' and in this context are attached sealingly to the adapter pieces 6' and the ends sealingly to the front housing section 1' and the drive housing 2 so that the drill chuck 3 with the clamping bodies 32 is positioned here within the bellows 6. When advancing the drilling needle 4, the bellows 6 will collapse wherein the adapter pieces 6' prevent buckling or deflection of the bellows 6 so that the drilling needle 4 is not impaired in its movement.

A special sealing action at the drilling needle through opening 5' is not provided and in this way water entry through the drilling needle through opening 5' is permitted so that the space within the bellows 6 around the drilling needle 4 can fill with moisture or water. Since the bellows 6 as well as their connections are designed to be watertight and coupling of the drill chuck 3 with the drive unit in the drive housing 2 is designed to be impermeable to water, as will be explained in the following, the electrical drive which is housed within the housing 1 and the device for acquiring the drilling resistance do not come into contact with moisture/water so that the function and measuring precision of the drilling resistance measuring device 10 are not impaired.

The volume of the bellows device upon advancing of the drilling needle 4 for performing the drilling resistance measurement is compressed and in this way increasing pressure is generated within the water volume contained in the bellows device. So that this pressure does not become too great and impair the advancing action of the drilling needle 4, a valve 13 is provided that, from a predetermined pressure on, allows water to exit from the interior of the bellows device. In the opposite direction, when after completion of the drilling resistance measurement the drilling needle is retracted, the valve 13 blocks in accordance with a non-return valve. Water or moisture can penetrate only through the drilling needle outlet opening 5'.

Figure 3:
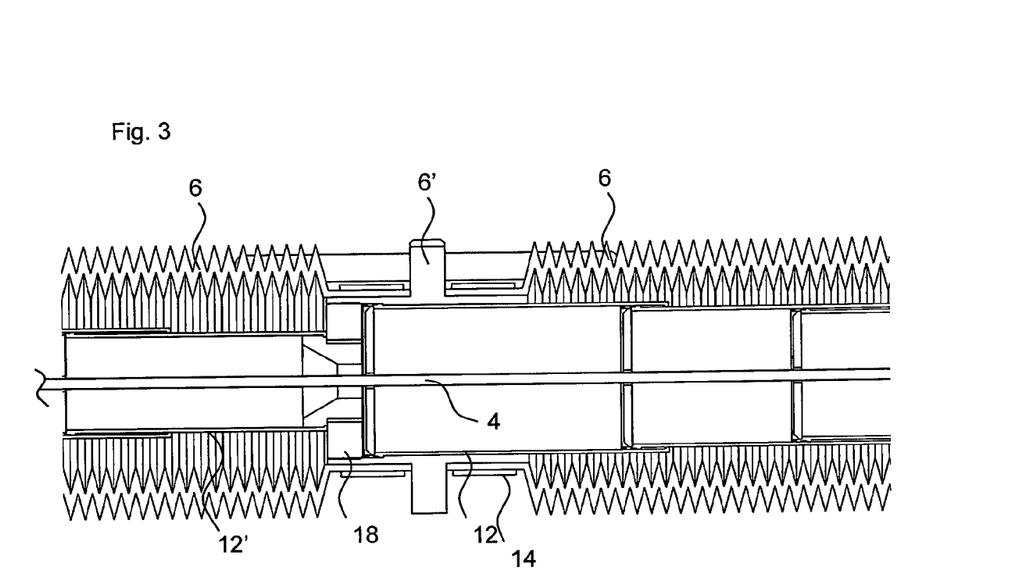
FIG. 3 a sectional side view of a coupling section of two bellows with a drilling needle extended through telescoping tube.

FIG. 3 illustrates a coupling section between two neighboring bellows 6. The adapter piece 6' is designed here as a hose coupler. The end sections of the bellows 6 which are not folded are attached seal-tightly by fastening devices 14, for example, hose or pipe clamps, on the hose coupler 6'. The stroke length of the sealed unit of bellows 6 and adapter piece 6' is predetermined but can be mounted in series one after another as often as needed, with a respective adapter piece 6' between neighboring bellows 6, so that all lengths—depending on the drilling needle length—can be realized.

FIG. 3 also shows that the drilling needle 4 within the bellows device is guided through telescoping tubes of which each one is comprised of several cup-shaped tube sections 12, 12'. Upon advancing of the drilling needle 4, the cups 12, 12' of each telescoping tube are pushed into each other. When, as in the present case, several telescoping tubes are used, in the area of the adapter pieces 6' of the bellows device a tube section 12' with smallest diameter of a first telescoping tube is resting on the bottom of the greatest tube section 12 of the neighboring telescoping tube. The arrangement of telescoping tubes and bellows device which is centered around the drilling needle 4 is assisted by a support 18 of the smallest telescoping tube section 12' in the adapter piece 6'. The telescoping tube is not sealed so that within the bellows 6 and thus also inside the telescoping tube arrangement around the drilling needle 4 moisture or water may be present because the one or more bellows 6 are sealed at the adapter pieces 6' as well as the drilling needle outlet guide 5 and the drill chuck 4.

Figure 4:
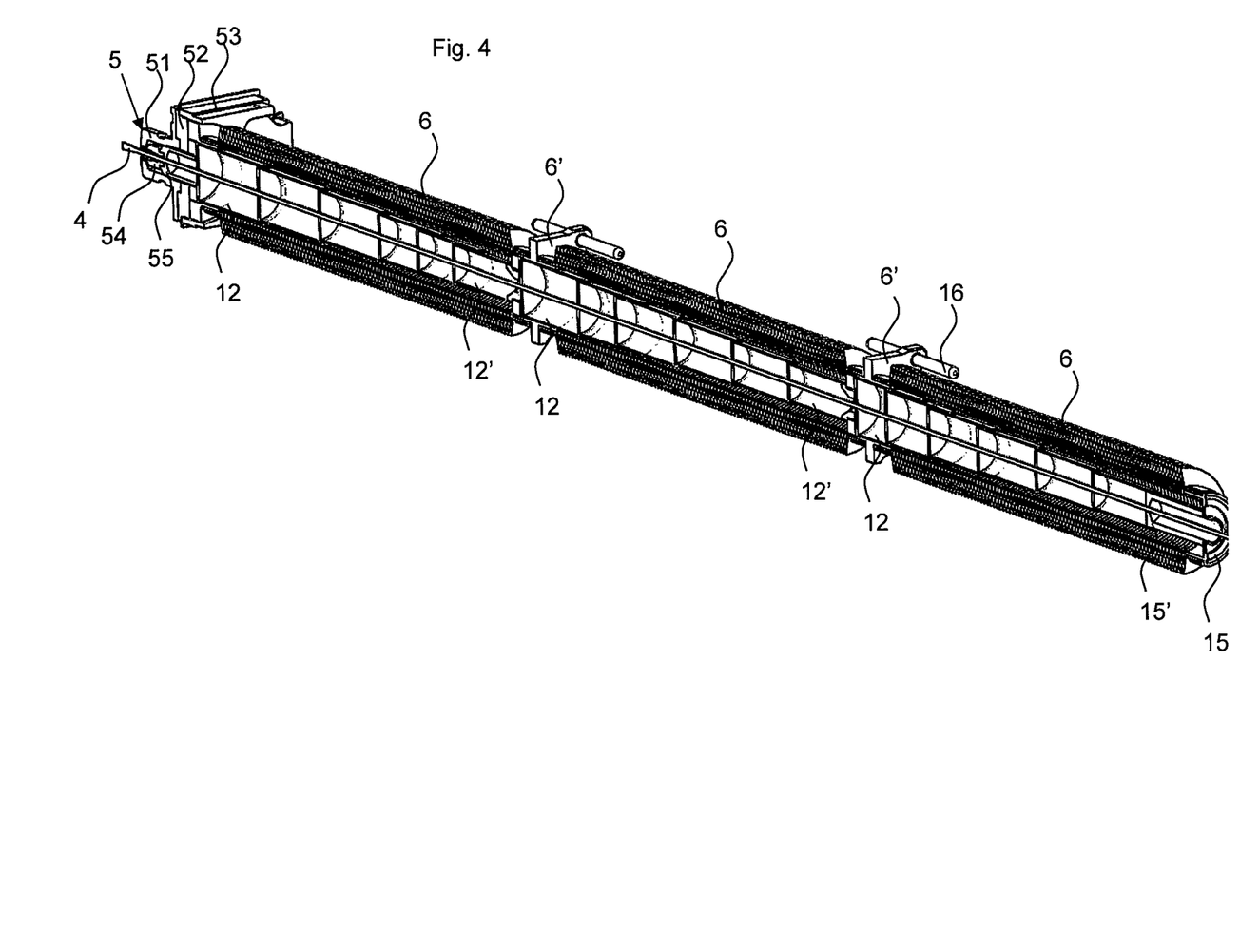
FIG. 4 a perspective sectional side view of a drilling needle surrounded by three bellows and guided by three telescoping tubes with drilling needle outlet guide.

As can be seen in FIG. 4, the drilling needle 4 can be surrounded by several telescoping tubes, i.e., by an elongated telescoping tube which is comprised of several telescoping sequences. The number of telescoping tubes and the number of respective cup-shaped tube sections 12, 12' depends, like the number of bellows/adapter piece units, on the length of the drilling needle 4. In the illustrated embodiment, the number of the telescoping tubes corresponds with the number of the bellows 6 wherein the adapter pieces 6' between two neighboring bellows 6 are arranged in the area of a tube section 12 with greatest diameter at the transition to the tube section 12' with smallest diameter of the neighboring telescoping tube. In the illustrated embodiment, a tube section 12 with greatest diameter is pointing to the working end of the telescoping tube and ends at the drilling needle outlet guide 5 where also the corresponding fold bellows 6 is attached sealingly. On the opposite end, the last tube section 15' is embodied as a docking sleeve together with the flange member 15, on which the last bellows 6 is attached, for seal-tight arrangement on the drive housing (FIG. 2) while the drilling needle 4 is received by the drill chuck (not illustrated in FIG. 4). The attachment of the last bellows 6 on the flange member 15 can be realized in the same way as on the adapter piece by a fastening device such as a hose clamp on the end section of the bellows 6 that is not folded.

In principle, it is however also possible to select the arrangement of the cup-shaped tube sections 12, 12' in reverse in relation to the tube section diameter, i.e., a cup with greatest diameter is positioned at the docking end and a cup with smallest diameter at the working end.

Figure 5:
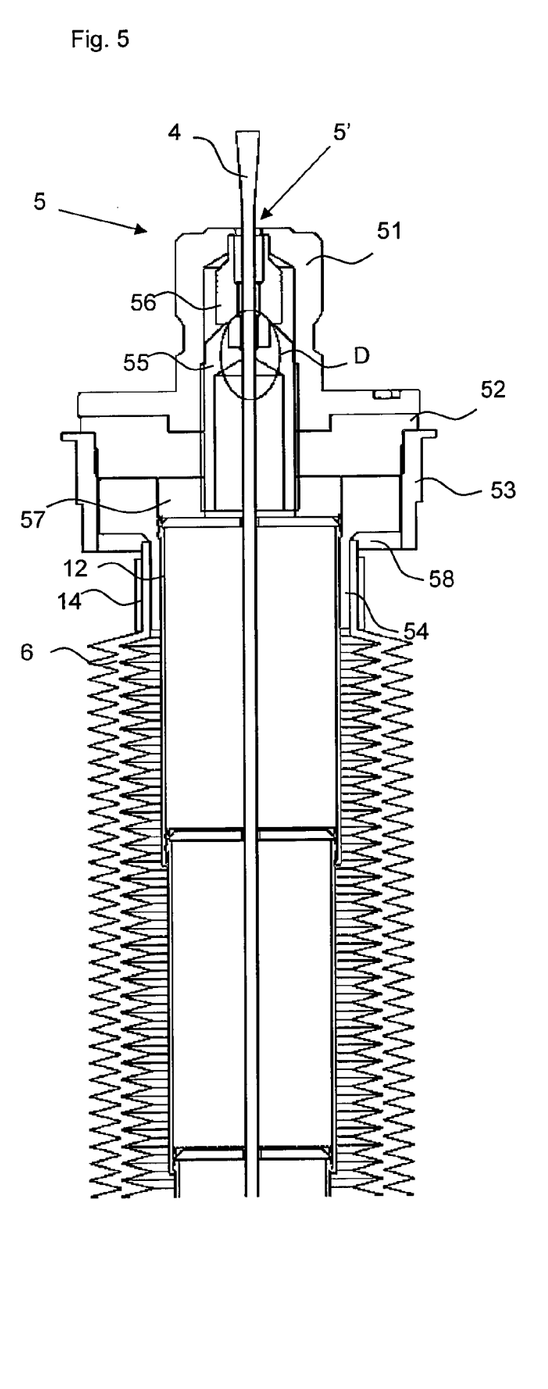
FIG. 5 a sectional side view of the connection of the bellows to the drilling needle outlet guide.
Figure 6:
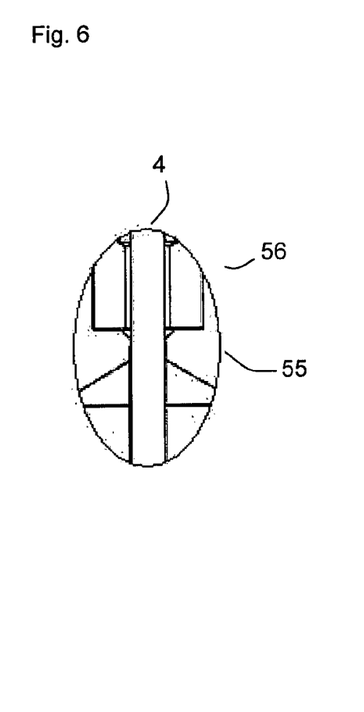
FIG. 6 an enlarged detail illustration of a section of the drilling needle outlet guide.

The configuration of the drilling needle outlet guide 5 is illustrated in FIG. 4 and more clearly in FIG. 5. Detail D of the drilling needle outlet guide 5 that shows a location where the diameter of the drilling needle 4 is almost identical to the diameter of a drilling needle through opening in the inner guide sleeve 55 is illustrated in FIG. 6. The diameter of the drilling needle 4 and the diameter of the slightly greater drilling needle through opening have only minimal play. Such a minimal tolerance range can be realized only due to the centered guiding of the drilling needle 4 in the drill chuck 3 (compare FIGS. 8 through 10) and thus substantially without sealing measures at this location.

The drilling needle outlet guide 5 is comprised here of an outer guide sleeve 51 with a screwed-in inner guide sleeve 55 and a bridging sleeve 56 which extends in the outer guide sleeve 51 between the inner guide sleeve 55 and the drilling needle outlet opening 5'. An annular flange 52 which is resting on the outer guide sleeve 51 and a telescoping stop 57 which is resting on the annular flange 52 are screwed one behind the other on the inner guide sleeve 55. A telescoping receiving sleeve 54 surrounds not only partially the last tubular section 12 but also the telescoping stop 57 and is resting on the annular flange 52. The section of the corresponding bellows 6 which is not folded is attached watertightly with an appropriate fastening device 14 on the cylindrical section of the telescoping receiving sleeve 54 which surrounds the tube section 12. The telescoping receiving sleeve 54 is attached by means of a screw ring 53 and a washer 58 on the annular flange 52.

Figure 7:
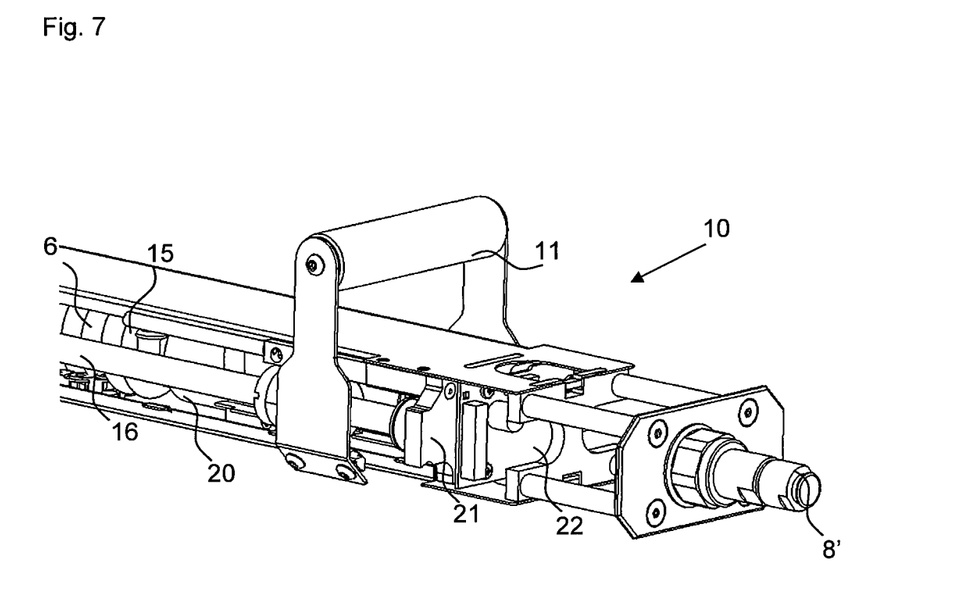
FIG. 7 a perspective view of the drive section of a drilling resistance measuring device.

FIG. 7 shows the section of the drilling resistance measuring device 10 which is facing away from the drilling needle outlet opening 5' where the docking flange 15 is resting on the drill chuck and where the drive for the drilling needle is housed which is connected with measuring and control devices as well as the connector 8'. The guiding or stabilization rod 16 which is shown also sectionwise at the adapter pieces 6' in FIG. 4 serves for a straight guiding action of the bellows 6 and the telescoping tubes when the latter upon advancement of the drilling needle 4 are pushed together or are pulled apart upon retraction of the needle. Optionally, this back-and-forth movement can be assisted actively by means of the guiding/stabilization rod 16 so that the telescoping tubes and the bellows 6 are moved actively and synchronously with the drilling needle 4.

In the following, details of the drilling needle receptacle on the drive housing 2 according to an embodiment of the drilling needle receptacle are described in relation to FIGS. 8 to 10. For reasons of simplification, in these Figures concerning a detail of the drilling needle receptacle no bellows device is illustrated.

Reference is being had to the complete disclosure of the German patent application DE 10 2013 015 131 of the applicant. The subject matter of the application DE 10 2013 015 131 is thereby incorporated into this application.

Figure 8:
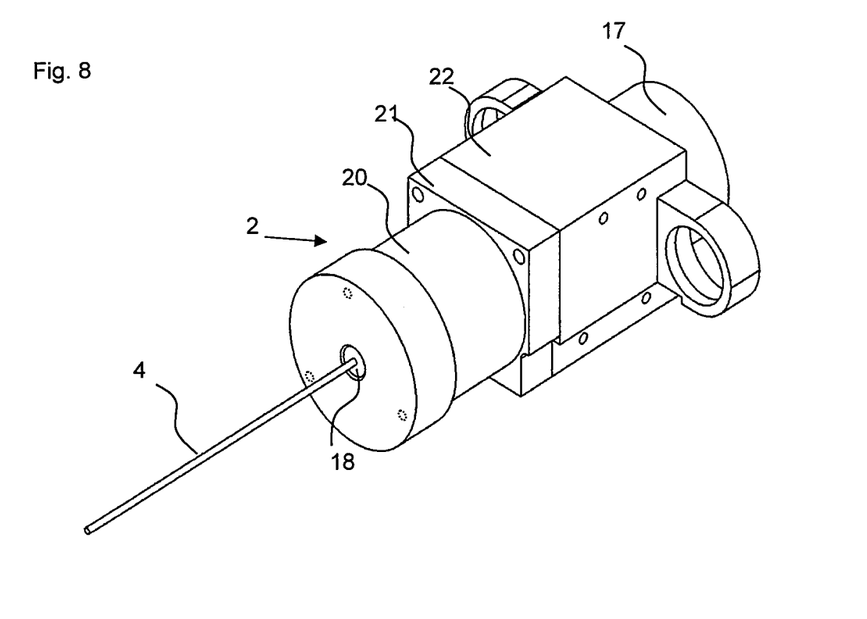
FIG. 8 a perspective detail view of a drilling needle receptacle at the drive housing.

The drilling needle receptacle illustrated in FIG. 8 comprises in the housing 22 a motor drive shaft which is connected with the motor 17 and which is coupled by means of a magnetic coupling (not illustrated) with the receiving element 30 (compare FIG. 9) for contact-free torque transmission onto the drilling needle 4 which is received in the receiving element 30 of the drill chuck 3. Due to the contact-free operative connection between drill chuck and drive, a water-tight sealing action at this location can be realized in a simple way.

In the receiving element 30, the flattened end section 4' of the drilling needle 4 (compare FIG. 10) is clamped by clamping bodies 32 and the clamping insert 31. The housing segment 21 surrounding the drive-associated coupling partner is connected with the motor housing 22, for example, by means of screws or pins.

The drilling needle 4 is secured against slip by means of the flattened end section 4' in the drilling needle receptacle; however, this flattened end section 4' causes a certain imbalance upon rotation of the drilling needle 4. In order to ensure despite of this a centered arrangement of the drilling needle 4, not only the contact-free magnetic coupling of the drilling needle receptacle with the drive device but also a contact-free arrangement of the receiving element 30 in the drill chuck 3 is provided. Moreover, the drilling needle 4 is supported by a guide sleeve 18 which is supported in the through opening of the front cover 2, is axially centered, and extends thus concentric with the motor drive shaft and the drilling needle outlet opening 5', independent of the eccentric displacements occurring at the receiving element 30 due to imbalance.

Such a drilling needle 4 has less of a tendency to break wherein the cross-sectional dimensions of the drilling needle 4 at a right angle to the flattened portion of the end section 4' is at most 5%, preferably 3%, smaller than the diameter of the drilling needle 4.

The front cover 2 illustrated in FIG. 8 can be provided, for example, at the circumferential inner wall with a thread with which it can be screw-connected to the housing section 20 which then is provided with an appropriate outer thread. Alternatively, the front cover 2 can also be non-detachably connected with the housing section 20, for example, can be adhesively connected. The housing section 20 is detachably connected with the housing segment 21. For this connection, for example, a thread on an inner circumferential section of the housing section 20 and on an outer circumference of a corresponding section of the housing segment 21 can be provided. Of course, also other embodiments of the housing components are conceivable.

For adjusting the axial distance between the magnetic coupling partners, not illustrated, the screw depth between housing section 20 and housing segment 21 can be simply varied which can be done manually or automatically with appropriate actuating means, or, for example, a housing section 20 with a different length can be used also. Further alternatives for adjusting the axial distance between the coupling partners reside in an axial adjustable connection of one or both coupling partners on the receiving element 30 and/or the drive shaft.

Accordingly, for exchange of the drill chuck 3, for which purpose the housing section 20 connected with the front cover 2 is detached from the housing segment 21, the same transmission of torque can be maintained by adjustment of the spacing of the two coupling partners.

Figure 9:
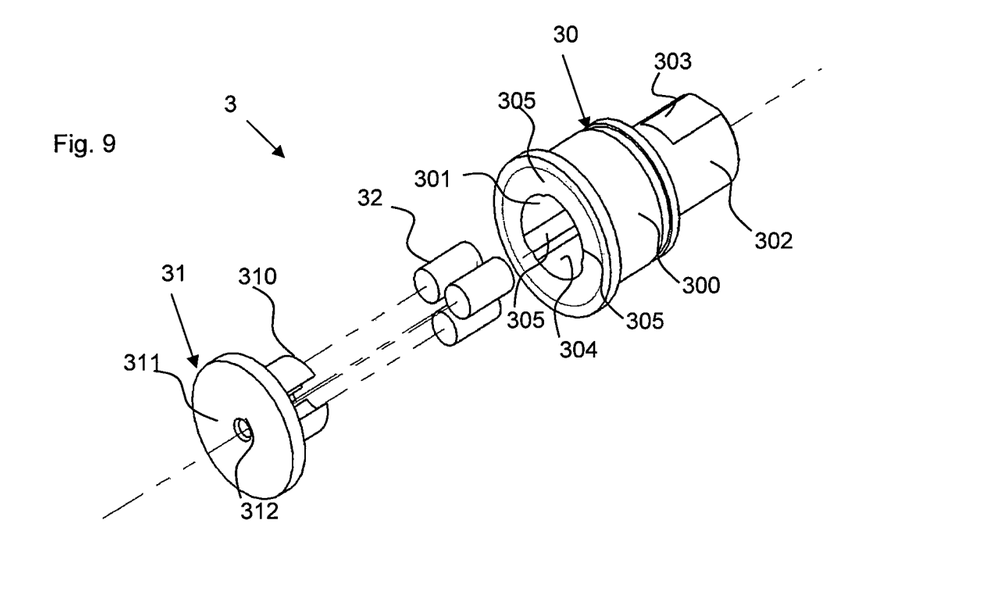
FIG. 9 a perspective exploded view of the drilling needle receptacle of FIG. 8.
Figure 10:
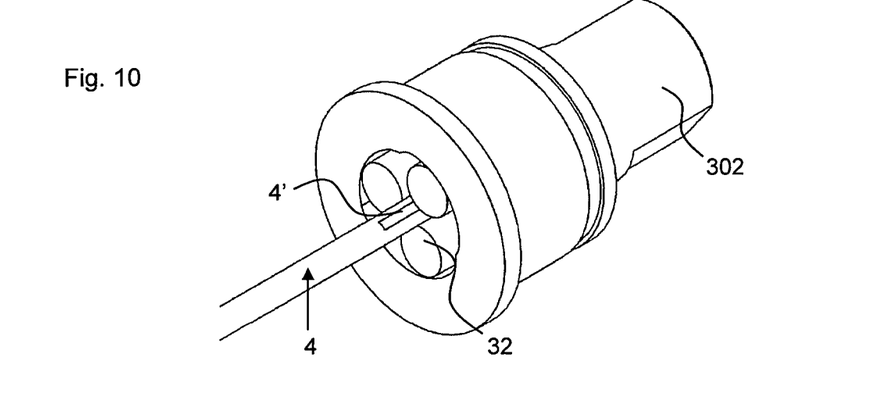
FIG. 10 a perspective detail view of the drilling needle receptacle of FIG. 9 with drilling needle.

FIGS. 9 and 10 show further details of the drilling needle receptacle. Here, the receiving element 30 is shown with the cylindrical section 300 that comprises the recess 301 and with the pin section 302 which is connected with one of the magnetic coupling partners. The pin section 302 comprises a flattened portion 303 for better engagement.

In accordance with the counter bodies 310 of the clamping insert 31 which supplement the three clamping bodies 32, the wall of the recess 301 is divided into three segments 304 which are delimited by the inwardly projecting stops 305. The contact disk 311 with which the clamping insert 31 contacts the end face of the cylindrical section 300 of the receiving element 30 comprises a central through opening 312 for the drilling needle 4 which, with its flattened end section 4', is clamped between the clamping bodies 32 and the counter bodies 310 in the recess 301.

The drilling needle 4 is received with the flattened end section 4' in the recess 301 of the receiving element 30 between the clamping bodies 32 and the counter bodies 310. The imbalance, which is caused by the flattened end section 4' upon rotation, is compensated in that one of the clamping bodies 32 within the cage which is formed of the counter bodies 310 of the clamping insert 31 performs respectively the clamping action of the drilling needle 4, depending on where the imbalance is presently occurring.

The wall segments 304 of the recess 301 deviate in their configuration from a centered circular profile wherein each wall segment 304 corresponds to a section of a spiral line around the drilling needle 4 so that the stops 305 each form the transition between a proximal and distal segment section of neighboring segments 304. When the clamping bodies 32 are moved into the distal segment sections their spacing to the drilling needle 4 is enlarged and the clamping engagement is released. Conversely, the drilling needle 4 is clamped between the clamping bodies 32 when they are moved in the direction of proximal segment sections.

The drilling needle receptacle illustrated in FIGS. 8 through 10 is to be understood as an example; the extent of protection of a drilling resistance measuring device according to the invention is not limited thereto. Other drill chuck embodiments, housing solutions, and coupling variance are conceivable without deviating from the extent of protection of the invention.

Figure 14:
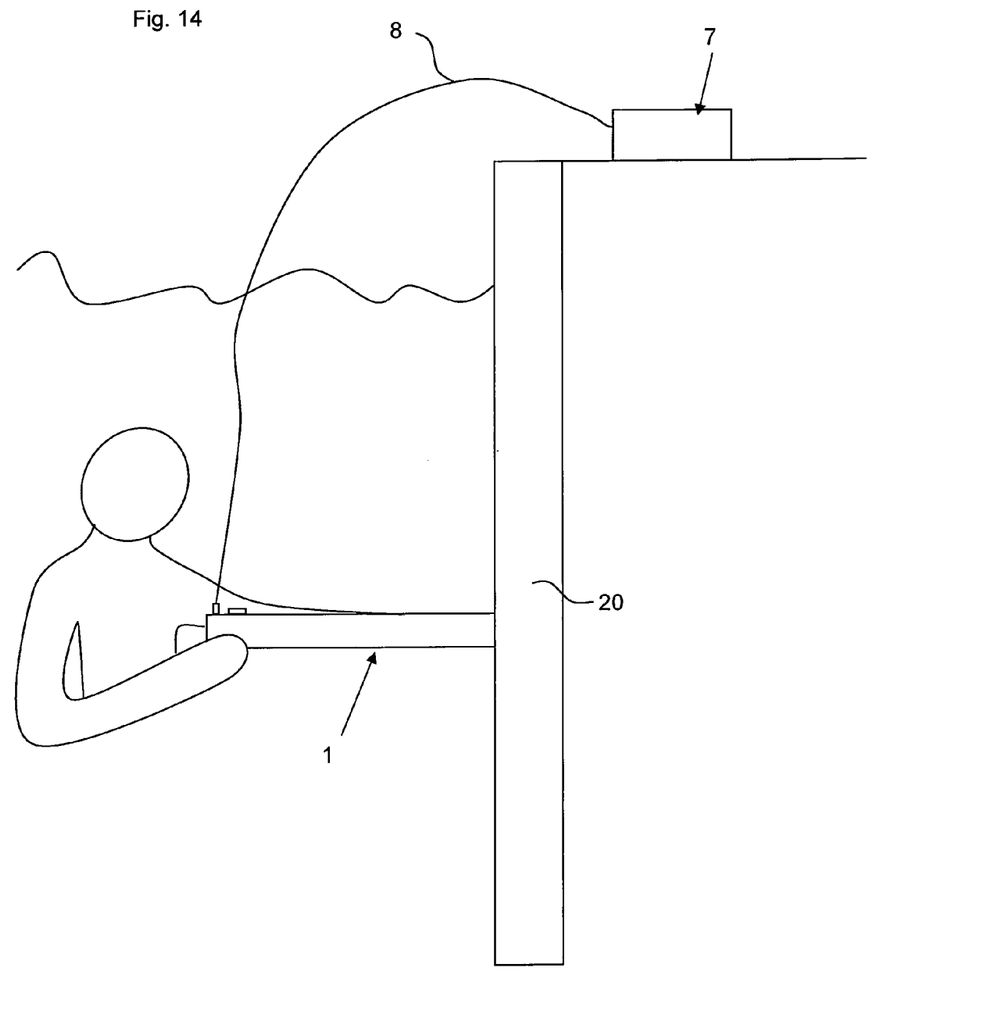
FIG. 14 a schematic illustration of a drilling resistance measuring device in use under water.

FIG. 14 shows a drilling resistance measuring device according to the invention in use. A diver performs the measurement on a test body 20 below the water line. Measured data are transmitted through the connecting cable 8 to the device 7 for evaluation, storage, and output which is positioned outside of the water. In deviation from the illustration, a wireless transmission of the measured data to the device 7 is conceivable also.

A drilling resistance measuring device according to the invention with which primarily drilling resistance measurements based on performance data of the motor are recorded can be indeed further developed according to DE 10 2009 013 069 A1/B4 of the applicant which is incorporated entirely herein by reference. In this context, the properties of column-shaped or cylindrical sections of test bodies are examined in that the drilling needle by means of a drilling device is introduced approximately at a right angle to the longitudinal axis of the section of the body to be examined in a discontinuous process, wherein, on the one hand, during insertion a drilling resistance measurement is performed and, on the other hand, recording of an impulse tomogram by discontinuous insertion is made possible in which the impulses that are thus generated are detected by sensors which are distributed around the circumference of the test body. The propagation rate of the impulse waves depends primarily on the density and hardness of the test body material on the path from the source to the different sensors. Accordingly, the drilling resistance measurement is supplemented by an impulse tomogram so that more information with regard to the interior of the test body can be obtained or a high precision image of the constitution of the core material is generated.

List of Reference Characters

| | | | |
|---|---|---|---|
| 1 | housing | 6 | bellows |
| 1' | front housing section | 6' | adapter piece |
| 2 | drive housing | 7 | computing device |
| | | 70 | rechargeable battery pack |
| 3 | drill chuck | 71 | locking section |
| 30 | receiving element | 72 | air filter |
| 300 | cylindrical section | | |
| 301 | recess | 8 | cable |
| 302 | pin section | 8' | connector |
| 303 | flattened portion | 80 | pneumatic hose |
| 304 | inner wall segments | 81 | counter locking section |
| 305 | stop | 82 | compressor |
| 31 | clamping insert | | |
| 310 | counter body | 9 | operating element |
| 311 | contact disk | 90 | display |
| 312 | through opening | | |
| 32 | clamping body | 10 | drilling resistance measuring device |
| 4 | drilling needle | 11 | grip |
| 4' | flattened end section | 12, 12' | telescoping tube sections |
| 13 | pressure valve | | |
| 5 | drilling needle outlet guide | 14 | fastening device |
| 5' | drilling needle outlet opening | 15 | docking flange |
| 51 | outer guide sleeve | 15' | docking telescoping tube section |
| 52 | annular flange | 16 | guide rod |
| 53 | screw ring | 17 | drive/motor |
| 54 | telescoping receiving sleeve | 18 | support |
| 55 | inner guide sleeve | | |
| 56 | bridging sleeve | 20, 21 | housing sections |
| 57 | telescoping stop | 22 | motor housing |
| 58 | washer | | |

What is claimed is:

1. Drilling resistance measuring device (10) for material testing in a humid environment or under water, wherein the drilling resistance measuring device (10) comprises a housing (1) in which a drive and a drill chuck (3), coupled with the drive and provided with a drilling needle (4) detachably arranged therein, are arranged,
    wherein the housing (1) comprises a drilling needle outlet opening (5') which is surrounded by a drilling needle outlet guide (5) and through which the drilling needle (4) extends out of the housing (1),
    wherein the drilling resistance measuring device (10) comprises at least one bellows (6) which is arranged in the interior of the housing (1) around the drilling needle (4) between the drill chuck (3) and the drilling needle outlet guide (5), wherein through the drilling needle outlet opening (5') moisture or water can enter the bellows (6), and wherein the connection between the bellows and the drill chuck is water-tight.

2. Drilling resistance measuring device (10) according to claim 1, wherein the at least one bellows (6) at one end is fastened sealingly around the drill chuck (3) to the drive housing (2) and with the other end is fastened sealingly around the drilling needle outlet opening (5') to the drilling needle outlet guide (5) or to the housing (1).

3. Drilling resistance measuring device (10) according to claim 1, wherein between the drill chuck (3) and the drilling needle outlet guide (5) at least two bellows (6) are arranged serially behind each other and are connected to each other by an adapter piece (6').

4. Drilling resistance measuring device (10) according to claim 1, wherein the drill chuck (3) and the drive are connected to each other by means of a coupling device that provides for a contact-free torque transmission from the drive to the drill chuck (3).

5. Drilling resistance measuring device (10) according to claim 4, wherein the receiving element (30) comprises at least one cylindrical section (300) with a recess (301) and the drill chuck (3) comprises at least one clamping body (32) and a clamping insert (31), wherein the clamping insert (31) comprises a counter body or bodies (310) supplementing the at least one clamping body (32) and extending away from the contact disk (311) that is contacting an end face of the cylindrical section (300) and that comprises a through opening (312) for the drilling needle (4), wherein the counter member or members (310) and the at least one clamping body (32) in regard to dimensions and shape are configured for arrangement in the recess (301) and for a clamping receiving action of the flattened end section (4') of the drilling needle (4) between the clamping body or bodies (32) and the counter bodies (310).

6. Drilling resistance measuring device (10) according to claim 4, wherein an annular magnet forms the hollow cylindrical magnetic holder and is arranged at a spacing and contact-free coaxially around the cylindrical section (300) of the receiving element (30).

7. Drilling resistance measuring device (10) according to claim 6, wherein a magnetically affectable distance ring surrounds the cylindrical section (300).

8. Drilling resistance measuring device (10) according to claim 4, wherein the coupling device is a magnetic coupling device in which a drive-associated magnetic coupling partner is in operative connection with a drill chuck-associated magnetic coupling partner that comprises a hollow-cylindrical magnetic holder for a receiving element (30) of the drill chuck (3) that is configured for detachably receiving a flattened end section (4') of the drilling needle (4).

9. Drilling resistance measuring device (10) according to claim 1, wherein the drilling resistance measuring device (10) comprises a valve device (13) that
between the interior of the at least one bellows (6) and the environment of the drilling resistance measuring device (10) forms a fluidic connection around the drilling needle outlet guide (5), and
opens in a direction for water escape from the interior of the at least one bellows (6) into the environment upon reaching a predetermined pressure in the interior of the at least one bellows (6) and blocks in the opposite direction at least up to a second predetermined pressure in the interior of the at least one bellows (6).

10. Drilling resistance measuring device (10) according to claim 9, wherein the fluidic connection is formed at the drilling needle outlet guide (5) or at the housing (1).

11. Drilling resistance measuring device (10) according to claim 1, wherein the drilling needle (4) is guided in a telescoping guiding device of a plurality of cup-shaped tube sections (12, 12') of different diameters, wherein the telescoping guiding device extends within the at least one bellows (6) around the drilling needle (4) between the drill chuck (3) and the drilling needle outlet guide (5).

12. Drilling resistance measuring device (10) according to claim 1, wherein the drilling needle outlet guide (5) comprises a guide sleeve (55) with a through opening in which the drilling needle (4) is guided without sealing means, wherein the through opening of the guide sleeve (55) is dimensioned such that a gap between the drilling needle (4) and the guide sleeve (55) has a width of at most 5% of the drilling needle diameter.

13. Drilling resistance measuring device (10) according to claim 12, wherein the width of the guide sleeve (55) is 1% to 2% of the drilling needle diameter.

14. Drilling resistance measuring device (10) according to claim 1, wherein the drilling resistance measuring device (10) comprises a rechargeable battery pack (70) for supply of the drive with electrical energy, wherein
the rechargeable battery pack (70) comprises an electrical connector and a locking section (71) and wherein
the drilling resistance measuring device (10) comprises a corresponding electrical connector and a corresponding counter locking section (81),
wherein
in an engaging arrangement the locking section (71) of the rechargeable battery pack (70) is in engagement with the counter locking section (81) of the drilling resistance measuring device (10) and the electrical connectors of the rechargeable battery pack (70) and of the drilling resistance measuring device (10) are in contact,
in a decoupled arrangement the locking section (71) of the rechargeable battery pack (70) is detached from the counter locking section (81) of the drilling resistance measuring device (10) and the electrical connector of the rechargeable battery pack (70) is connected by a cable (8) with the electrical connector of the drilling resistance measuring device (10).

15. Drilling resistance measuring device (10) according to claim 1, wherein the drilling resistance measuring device (10) in the drive section comprises a compressor (82) for providing an overpressure in the housing (1) which is connected with an air filter (72).

16. Drilling resistance measuring device (10) according to claim 15, wherein the air filter (72) is arranged at the rechargeable battery pack (70), wherein the rechargeable battery pack (70) and the housing (1) comprise pneumatic connectors which, in the engaging arrangement of the rechargeable battery pack (70), are connected with each other or, in the decoupled arrangement of the rechargeable battery pack (70), are connected by a hose (80) with each other.

17. Method for drilling resistance measurement with a drilling resistance measuring device according to claim 1, comprising the steps:
attaching the drilling resistance measuring device (10) in humid environment or under water to an object (20) to be tested, in doing so
allowing moisture or water to penetrate through the drilling needle outlet opening (5') into the at least one bellows (6);
advancing and inserting the drilling needle (4) into the object (20) to be tested, in doing so pushing together the at least one bellows (6), and, upon reaching a predetermined pressure within the pushed-together bellows (6), allowing moisture or water to exit into the environment of the drilling resistance measuring device (10);
measuring a power input or current consumption used by the drive in inserting the drilling needle into the object;
measuring a penetration depth of the drilling needle into the object;
determining the drilling resistance of the object based on the penetration depth and the power current.

18. The method according to claim 17, wherein moisture or water is allowed to exit into the environment by opening a valve device (13) which is in communication with the interior of the at least one bellows (6) and the environment.

* * * * *